US011957887B2

(12) United States Patent
Bucher

(10) Patent No.: US 11,957,887 B2
(45) Date of Patent: Apr. 16, 2024

(54) COMPLIANT TRANSMISSION SYSTEM

(71) Applicant: Technion Research & Development Foundation Limited, Haifa (IL)

(72) Inventor: Izhak Bucher, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 893 days.

(21) Appl. No.: 17/013,603

(22) Filed: Sep. 6, 2020

(65) Prior Publication Data

US 2021/0052821 A1    Feb. 25, 2021

Related U.S. Application Data

(63) Continuation of application No. PCT/IL2019/050259, filed on Mar. 8, 2019.

(60) Provisional application No. 62/640,198, filed on Mar. 8, 2018.

(51) Int. Cl.
*A61M 5/315* (2006.01)

(52) U.S. Cl.
CPC . *A61M 5/31583* (2013.01); *A61M 2205/0216* (2013.01); *A61M 2205/04* (2013.01); *A61M 2205/273* (2013.01)

(58) Field of Classification Search
CPC ...... A61M 5/31583; A61M 2205/0216; A61M 2205/04; A61B 2017/00345
See application file for complete search history.

(56) References Cited

U.S. PATENT DOCUMENTS

| 4,435,173 | A | | 3/1984 | Siposs et al. |
| 4,625,582 | A | | 12/1986 | Kiryu |
| 4,713,985 | A | | 12/1987 | Ando |
| 5,345,925 | A | | 9/1994 | Allred, III et al. |
| 5,653,692 | A | * | 8/1997 | Masterson ............ A61B 18/08 |
| | | | | 604/113 |
| 6,702,830 | B1 | * | 3/2004 | Demarais ............. A61M 29/02 |
| | | | | 606/159 |
| 10,094,367 | B2 | | 10/2018 | Bucher et al. |
| 2013/0216400 | A1 | | 8/2013 | Bucher et al. |

FOREIGN PATENT DOCUMENTS

WO    WO 2019/171387    9/2019

OTHER PUBLICATIONS

International Preliminary Report on Patentability dated Sep. 17, 2020 From the International Bureau of WIPO Re. Application No. PCT/IL2019/050259. (8 Pages).
International Search Report and the Written Opinion dated May 28, 2019 From the International Searching Authority Re. Application No. PCT/IL2019/050259. (11 Pages).
(Continued)

*Primary Examiner* — Bradley J Osinski

(57) ABSTRACT

A compliant transmission system includes a rotatable wave generator and a sleeve fitted on the wave generator. The rotatable wave generator has an external surface including pattern extending both annularly and in a longitudinal direction. The sleeve is configured to be deformable and to be impressed on its outer surface with waves extending along the longitudinal direction during rotation of the pattern of the wave generator within the sleeve.

25 Claims, 13 Drawing Sheets
(6 of 13 Drawing Sheet(s) Filed in Color)

(56) References Cited

OTHER PUBLICATIONS

Davis et al. "Realization of An Automatic, Contactless, Acoustic Levitation Motor Via Degenerate Mode Excitation and Autoresonance", Sensors and Actuators A: Physical, 276: 34-42, Jun. 15, 2018.
Hagedorn et al. "The Importance of Rotor Flexibility in Ultrasonic Traveling Wave Motors", Smart Materials and Structures, 7(3): 352-368, Jun. 1998.
Harmonic Drive "Harmonic Drive Gearing: Principle of Operation: Strain Wave Gear Principle", Harmonic Drive, YouTube, Oct. 26, 2011.
Howell et al. "Handbook of Compliant Mechanisms", Wiley & Sons, p. 1-324, 2013.
Setter et al. "Propulsion at Low Reynolds Number by Multiple Traveling Waves", Proceedings of the Institution of Mechanical Engineers, Part C: Journal of Mechanical Engineering Science, 228(16): 2938-2949, Published Online Feb. 12, 2014.
Setter et al. "Robotic Swimmer/Pump Based on An Optimal Wave Generating Mechanism", Mechanism and Machine Theory, 70: 266-277, Available Online Aug. 23, 2013.
Wallaschek "Contact Mechanics of Piezoelectric Ultrasonic Motors", Smart Materials and Structures, 7(3): 369-381, Jun. 1998.
Zhao "Ultrasonic Motors: Technologies and Applications", Science Press Beijing, Chaps.1-15: 1-494, 2011. (Part I).
Zhao "Ultrasonic Motors: Technologies and Applications", Science Press Beijing, Chaps.1-15: 1-494, 2011. (Part II).
Zhao "Ultrasonic Motors: Technologies and Applications", Science Press Beijing, Chaps.1-15: 1-494, 2011. (Part III).

\* cited by examiner

COMPLIANT TRANSMISSION SYSTEM

RELATED APPLICATIONS

This application is a US Continuation of PCT Patent Application No. PCT/IL2019/050259 having international filing date of Mar. 8, 2019 which claims the benefit of priority under 35 USC § 119(e) of U.S. Provisional Patent Application No. 62/640,198 filed on Mar. 8, 2018. The contents of the above applications are all incorporated by reference as if fully set forth herein in their entirety.

FIELD AND BACKGROUND OF THE INVENTION

The present invention, in some embodiments thereof, relates to mechanical transmission and, more particularly, but not exclusively, to a compliant transmission system for a linear propulsion apparatus.

There is an ongoing need both in the mechanical instrument industry as well as in the medical devices industry for robotics-based motoring devices capable of producing prescribed motions efficiently and at relatively low cost. There is also an ongoing need for such robotic based motoring devices to be disposable. In some applications it is desirable to use such a motoring device in an enclosure such as a tube through which an element is to be controllably advanced in a linear direction. In small diameter applications such as for controlled fluid delivery through a syringe, a motor device would be required to deliver relatively large forces, e.g. 20-40 N while having small dimensions (10 mm diameter) so that it fits into the syringe. In implantable devices or miniature device for automatic drug delivery, the dimensions of the motoring device would be required to be even smaller. Instead, available products are known to be large, bulky and by no means disposable.

Compliant mechanisms are monolithic constructs capable of producing prescribed motions with no friction, backlash or bearings. Furthermore, soft robotics based motoring devices that include compliant mechanisms are sometimes designed to produce motion and force rather than to excel in power efficiency.

U.S. Pat. No. 10,094,367 entitled "Method and System for generating Mechanical Waves," the content of which is incorporated by reference herein describes a system for generating a mechanical wave. The system comprises a camshaft having plurality of rotatable cams, serially mounted on a shaft along an axis of an elastic tubular shell to form a varying phase angle along the shaft. The system further comprises a plurality of cam followers arranged circumferentially about each cam, such that a rotary motion of the cams generates a linear motion of the cam followers to radially bias in internal wall the shell. The variation of the phase angle is selected to generate a three-dimensional traveling wave along the shell.

SUMMARY OF THE INVENTION

According to an aspect of some example embodiments there is provided a compliant transmission system configured to provide linear propulsion through a tubular enclosure, a cylindrical enclosure or conduit such as but not limited to a tube and/or pipe. Optionally, compliant transmission system is configured to provide linear propulsion through an open channel or even along a flat surface, e.g., the compliant transmission system may walk along a surface. According to some example embodiments, the compliant transmission system includes a wave generator that is fitted within a deformable sleeve. The compliant transmission system is sized to engage an inner surface of a tubular enclosure through which it is to advance. In use, the compliant transmission system is inserted in the tubular enclosure and the wave generator is rotated with a motor. Rotation of the wave generator impresses a wave on the deformable sleeve and actuates the movement through the tubular enclosure.

According to an aspect of some example embodiments there is provided a linear propulsion apparatus configured for propulsion through a tubular enclosure. According to some example embodiments, the linear propulsion apparatus includes a rotational actuator coupled with the compliant transmission system described herein. In some example embodiments, the linear propulsion apparatus is a self-propulsion apparatus. Optionally, the self-propulsion apparatus is fully contained within the tubular enclosure. In alternate example embodiments, the rotational actuator is externally controlled.

According to an aspect of some example embodiments there is provided a disposable drug delivery system that is controllably actuated with the linear propulsion apparatus described herein. Optionally, the disposable drug delivery system is an automated system that is configured to controllably deliver a drug without human intervention based on movement of the linear propulsion apparatus. Optionally, the disposable drug delivery is configured to deliver the drug through a standard syringe and the linear propulsion apparatus is sized to fit within a barrel of the standard syringe and drive the plunger of the syringe. Optionally, the disposable drug delivery system is an implantable automatic drug delivery system including the linear propulsion apparatus described herein and further miniaturized so as to be configured to be integrated within the implantable device.

According to an aspect of some example embodiments, there is provided a compliant transmission system comprising: a rotatable wave generator having on an external surface thereof a pattern extending both annularly and in a longitudinal direction; and a sleeve fitted on the wave generator, wherein the sleeve is configured to be deformable and to be impressed on its outer surface with waves extending along the longitudinal direction during rotation of the pattern of the wave generator within the sleeve.

Optionally, the compliant transmission system is sized to fit into a tubular enclosure, wherein the outer surface of the sleeve is in physical contact with an inner wall of the tubular enclosure and wherein the wave impressed on the sleeve and the contact of the sleeve with the inner wall of the tubular enclosure are selected to impart a relative linear motion between the enclosure and the compliant transmission system.

Optionally, the physical contact between the sleeve and the inner wall is configured to lock the complaint transmission system in place absent rotation of the wave generator.

Optionally, the wave generator is a rod shaped element, and wherein the pattern comprises a raised helical thread extending around the rod and in the longitudinal direction.

Optionally, the wave generator comprises a connector configured to fixedly connect with a rotational actuator.

Optionally, the wave generator is formed of a rigid material.

Optionally, the wave generator is formed of a polymer material.

Optionally, the sleeve is configured to deform elastically during the rotation of the wave generator.

Optionally, the outer surface of the sleeve includes a pattern of protruding teeth.

Optionally, the pattern of protruding teeth extends along both the longitudinal.

Optionally, the pattern of protruding teeth is a helix.

Optionally, the wave generator comprises an array of cams positioned on an axle and wherein the relative phase angle between the array of cams is configured to define the pattern on the external surface of the wave generator.

Optionally, each of the cams in the array includes bearings fitted on the outer surface of the wave generator to reduce the friction between the wave generator and the sleeve during rotation.

Optionally, the sleeve includes a pattern of elongated protruding elements extending from an outer surface of the sleeve, wherein a length of the elongated protruding elements extending from the outer surfaces is 3-10 times longer than a diameter of the protruding elements.

According to an aspect of some example embodiments, there is provided a linear propulsion apparatus comprising: the compliant transmission system as described herein; and a rotational actuator coupled to the complaint transmission system.

Optionally, the linear propulsion apparatus is configured to impart a relative linear motion between a tubular enclosure and the compliant transmission system and wherein both the compliant transmission system and the rotational actuator are sized to fit into the tubular enclosure.

Optionally, the linear propulsion apparatus is configured to be self-propulsion apparatus.

Optionally, the rotational actuator is sized to be contained within the tubular enclosure.

Optionally, the rotational actuator is external to the tubular enclosure and coupled to the wave generator with an axle mounted on the rotational actuator.

Optionally, the rotational actuator is a direct current (DC) motor or piezo motor.

According to an aspect of some example embodiments, there is provided a disposable drug delivery system comprising: a tubular enclosure containing a drug to be delivered; a movable wall configured to displace the drug contained in the tubular enclosure; an outlet through which the drug contained in the tubular enclosure is dispensed; and a linear propulsion apparatus according as described herein configured to move the movable wall.

Optionally, the tubular enclosure, the movable wall and the outlet elements of a syringe and wherein the linear propulsion apparatus is configured to drive dispensing of the drug through the syringe.

Optionally, the linear propulsion apparatus is a self-propulsion apparatus.

Optionally, the disposable drug delivery system is configured to be implantable in a human body.

Optionally, the tubular enclosure is a glass tube.

According to an aspect of some example embodiments, there is provided a method of linear propulsion within a tubular enclosure, the method comprising: positioning a compliant transmission system into a tubular enclosure, wherein the compliant transmission system comprises a wave generator and a sleeve fitted on the wave generator, wherein the both the wave generator and the sleeve extend in a longitudinal direction and wherein an outer surface of the sleeve is flush with an inner surface of the tubular enclosure; rotating the wave generator with respect to the sleeve; generating waves on the sleeve that extend along the longitudinal direction; and inducing relative linear motion between the sleeve and the tubular enclosure based on the waves that have been generated.

Optionally, the method includes fixating the tubular enclosure to an external structure such that the wave pattern on the outer surface of the sleeve effects linear motion of the sleeve within the enclosure without effecting rotation or translation on the enclosure.

Optionally, the compliant transmission system is as described herein.

Optionally, the wave generator is rotated with a rotational actuator that is positioned within the tubular enclosure.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified blow-up drawing of an example linear propulsion apparatus for propulsion within a conduit in accordance with some example embodiments;

FIG. 2 is a simplified schematic drawing of an example compliant transmission system including a deformable sleeve with a generally smooth outer surface, in accordance with some example embodiments;

FIG. 3 is a simplified schematic drawing of an example compliant transmission system including a deformable sleeve with a patterned outer surface in accordance with some example embodiments;

FIG. 4A is a simplified schematic drawing of an example deformable sleeve including helically arranged array of teeth in accordance with some example embodiments;

FIG. 4B is a simplified schematic drawing of an example wave generator having a helical outer surface for a compliant transmission system in accordance with some example embodiments;

FIG. 5A is a simplified blow up schematic drawing of a tubular enclosure and an example compliant transmission system including a deformable sleeve with teeth arranged in a helical pattern in accordance with some example embodiments;

FIGS. 5B and 5C are simplified schematic blow up and cross sectional view schematic drawings respectively of a linear propulsion apparatus in accordance with some example embodiments;

FIG. 6 is a simplified schematic drawing showing an example wave motion of a portion of the compliant transmission system actuating linear self-propulsion within a conduit in accordance with some example embodiments;

FIG. 7 is a simplified schematic drawing showing a simulation demonstrating deformations of an elastic sleeve based on the azimuth orientation of the helix within the elastic sleeve in accordance with some example embodiments;

FIGS. 8A, 8B and 8C are simplified schematic drawings of a compliant transmission system including a camshaft in accordance with some example embodiments;

FIGS. 9A and 9B are schematic drawings of an array of cams shown in a perspective view and a side view, respectively, both in accordance with some example embodiments; and FIG. 10 is a schematic drawing of example elliptical paths that tips of legs on an outer surface of a deformable sleeve may create while moving along a surface in accordance with some example embodiments;

Figure 11A:
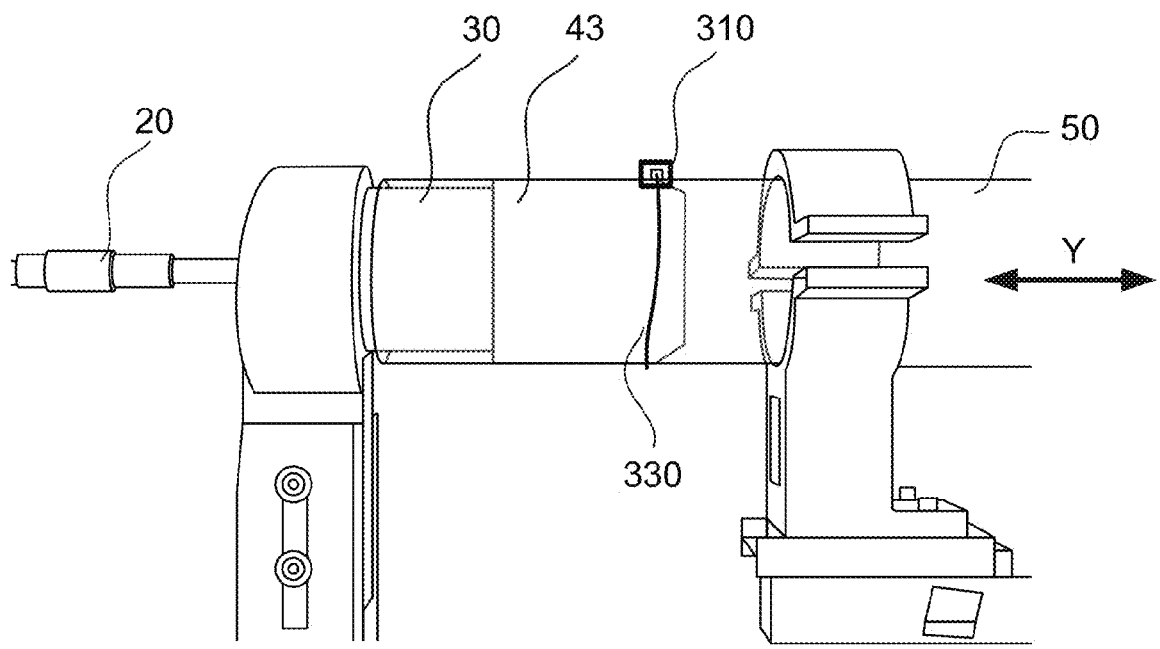
Figure 11B:
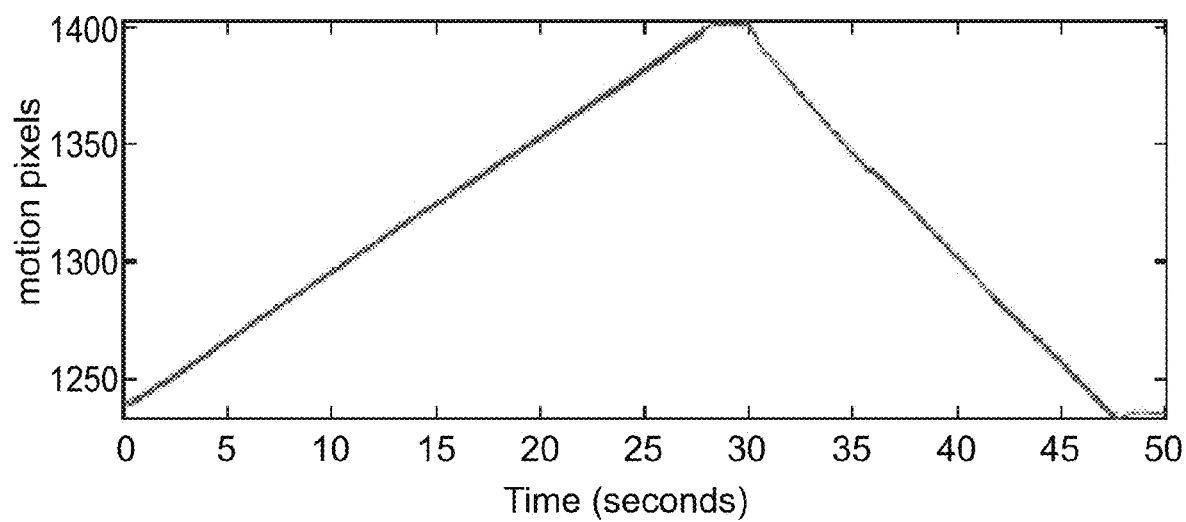
Figure 12A:
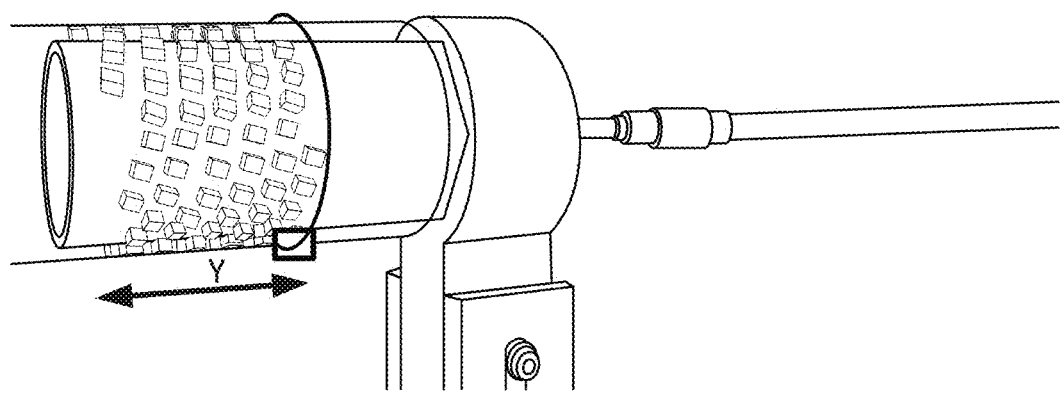
Figure 12B:
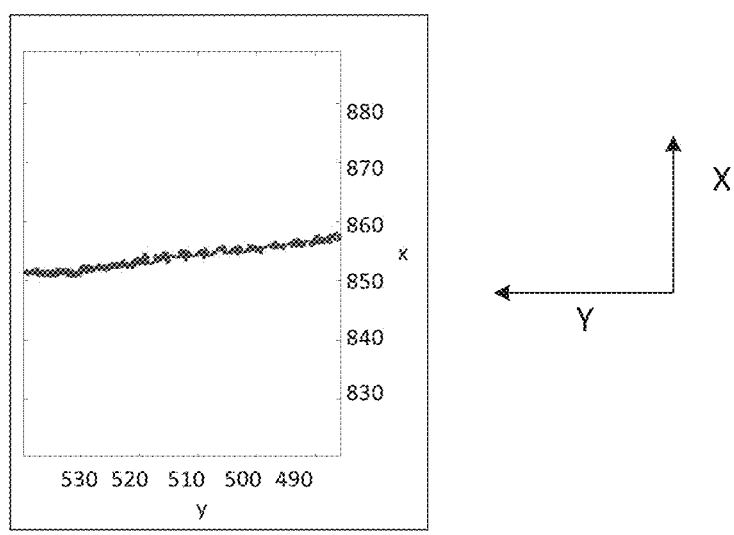
Figure 12C:
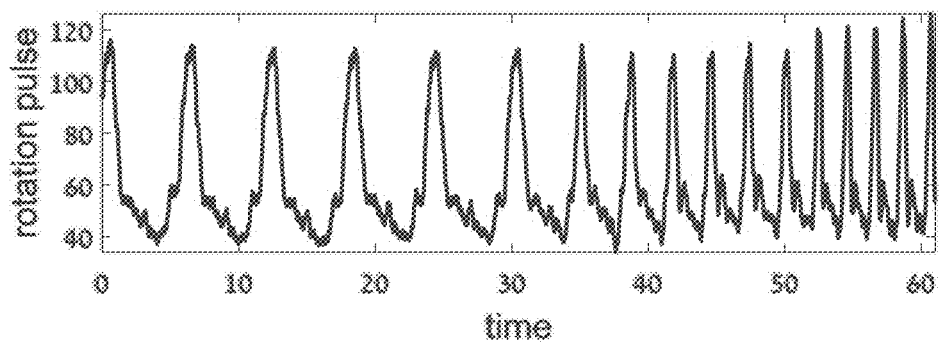
Figure 13A:
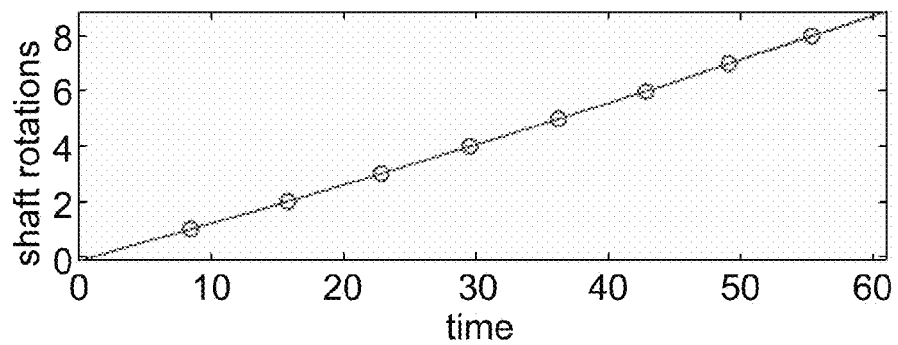
Figure 13B:
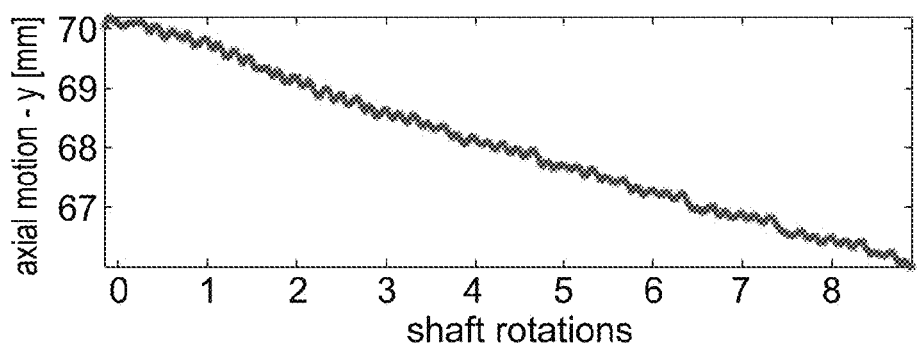
Figure 13C:
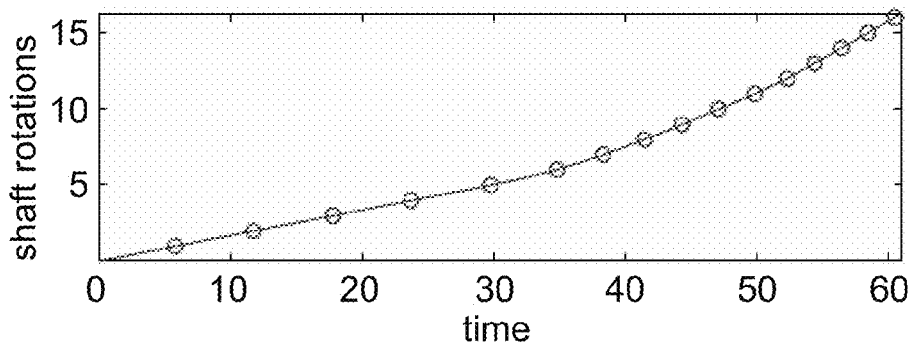
Figure 13D:
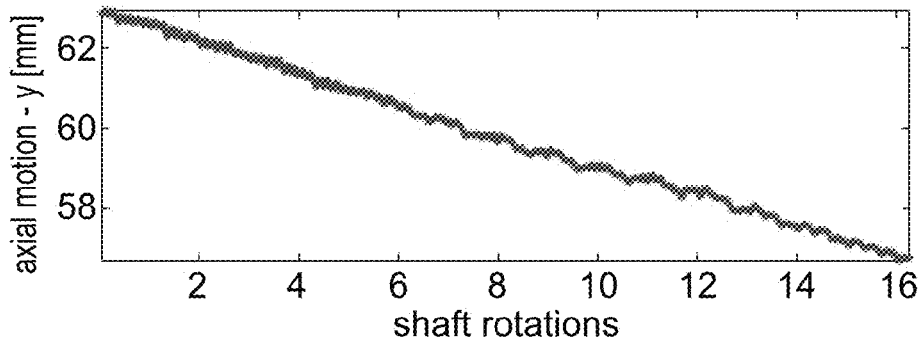
Figure 14A:
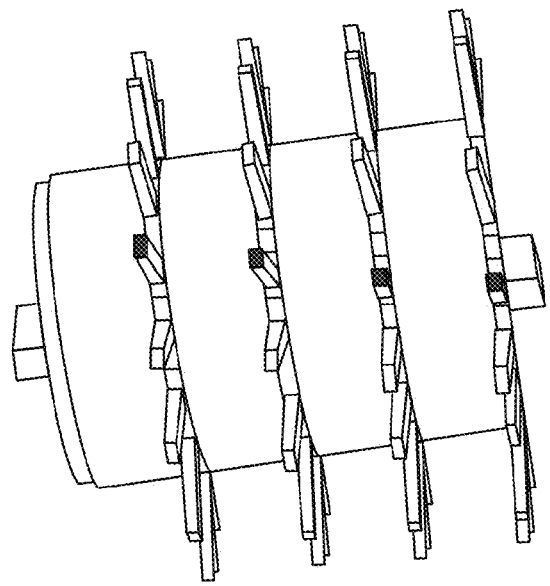
Figure 14B:
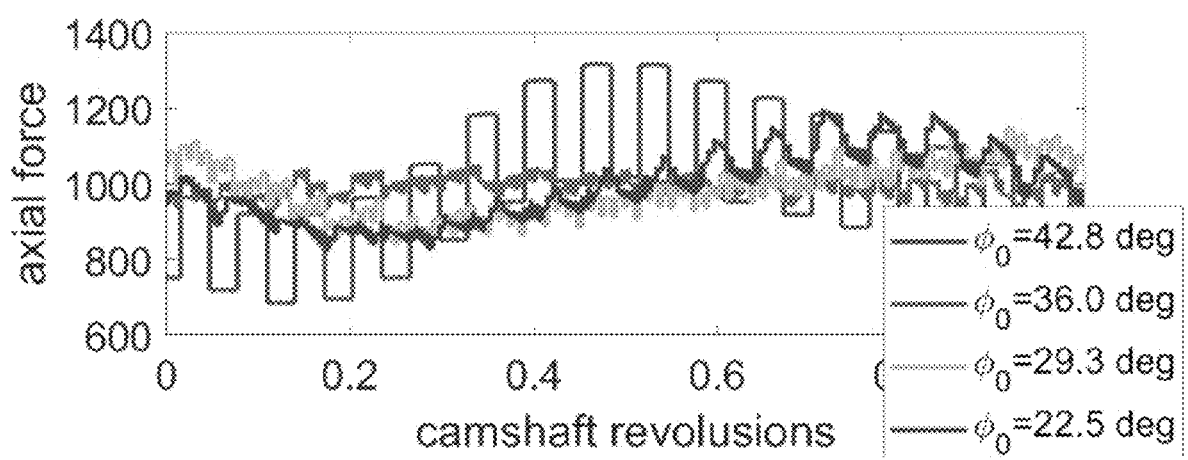

FIGS. 11A and 11B are an image of an experimental setup (FIG. 11A) to track linear propulsion with an example linear propulsion apparatus, and corresponding detected results (FIG. 11B) in accordance with some example embodiments;

FIGS. 12A, 12B and 12C are an image of another experimental setup to track linear propulsion with an example linear propulsion apparatus (FIG. 12A), and corresponding detected results (FIGS. 12B and 12C) in accordance with some example embodiments;

FIGS. 13A, 13B, 13C and 13D are example graphs showing axial motion as a function of shaft rotations for two different rotation profiles, all in accordance with some example embodiments; and FIGS. 14A and 14B are a schematic drawing of an example compliant transmission system including four cam sections, and an example graph showing effect of relative rotation (phase shift) between each of the four cam sections on the uniformity of the motion, all in accordance with some example embodiments.

DESCRIPTION OF SPECIFIC EMBODIMENTS OF THE INVENTION

The present invention, in some embodiments thereof, relates to mechanical transmission and, more particularly, but not exclusively, to a compliant transmission system for a linear propulsion apparatus.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

According to some example embodiments, the compliant transmission system includes a wave generator and an elastic sleeve. In some example embodiments, the wave generator is a rigid plug including a protruding pattern that is configured to form a wave pattern over a surface of the deformable sleeve when rotated within the deformable sleeve. According to some example embodiments, during operation, the compliant transmission system is introduced into a tubular enclosure in which an outer surface of the deformable sleeve with the wave generator fitted inside the sleeve engages an inner wall of the enclosure. Friction forces between the outer surface of the sleeve and the inner wall of the enclosure induce a relative linear motion between the sleeve and the enclosure, by means of a time-varying wave pattern generated by the wave generator while being rotated, e.g. with a rotating actuator. Optionally, the compliant transmission system is sized to be fitted inside the enclosure with a defined pre-load.

The wave generator may be configured to bias against the inner wall of the deformable sleeve in a manner that induces deformation waves on the outer surface of the deformable sleeve as the wave generator is rotated based on the protruding pattern of the wave generator optionally and preferably without inducing rotation of the deformable sleeve. In some embodiments of the present invention, the tubular enclosure is fixated to an external structure such that the wave pattern on the outer surface of the deformable sleeve effects linear motion of the apparatus within the enclosure without effecting rotation or translation on the enclosure. The deformations waves may be envelope waves that produce an advancing wave along longitudinal direction of the deformable sleeve. According to some example embodiments, kinetic integration between parts of the compliant transmission system is configured to create a large transmission ratio. Transmission ratio may be defined herein as an axial step of a point on the outer surface of the deformable sleeve per rotation of the wave generator. A large transmission ratio as defined herein is a transmission ratio of at least 20 or 30 micrometer per revolution, e.g. 34 micrometers. In some example embodiments, the transmission ratio may reach 5 millimeters per rotation or more depending on the defined parameters of the compliant transmission system.

According to some example embodiments, each of the wave generator and sleeve may be formed as a single part from a polymer, rubber and/or silicon and may be manufactured by standard three dimensional printing and/or injection molding processes. According to some example embodiments, the deformable sleeve is made of a material that is elastic over the expected working range of the sleeve. In some examples, the wave generator may be alternatively formed from metal or ceramic material.

According to some example embodiments, the protruding pattern on the wave generator is a helix pattern. Alternatively, the protruding pattern may be other periodic patterns defined by a Fourier series. The protruding pattern may typically be defined to propagate a full period of a wave over one rotation of the wave generator. In some example embodiments, the deformable sleeve is configured with a smooth outer surface. In other example embodiments, a pattern of teeth or protrusions is formed on the outer surface of the sleeve. The present inventor has found that adding the array of teeth and optionally orienting the array in relation to the wave generating pattern may increase a step size of the linear propulsion per rotation of the actuator, thereby increasing the impact applied by the apparatus. Optionally, size, pitch and spatial pattern of teeth are selected based on a desired step size of the linear propulsion per rotation of the actuator. For example, the wave generator and the orientation of the teeth may be selected with an emphasis on uniform axial force and/or may be selected to provide a defined transmission ratio. Optionally, the pattern of teeth may be aligned with a wave front produced by the wave generator so that the teeth may be deflected simultaneously during rotation of the wave generator. Aligning the teeth in this manner may increase the transmission ratio achieved. By controlling the geometrical parameters, the level of preload due to overlap between parts, the ratio of holding force and transmission ratio may be selected.

According to some additional example embodiments, the wave generator is a cam shaft with an array of cams that press the deformable sleeve against its tubular enclosure and together induce deformation waves on the deformable sleeve. Optionally, the cams include bearings configured to reduce friction between the rotating cams and the deformable sleeve. In some example embodiments, the linear propulsion apparatus including the wave generator formed from an array of cams may be used for induce propulsion in highly viscous or low Reynolds number environments, e.g. suitable for micro-scale swimming robots.

In some example embodiments, the deformable sleeve may include relatively long protrusions on its outer surface that generally look like hair protrusions. Optionally, relatively long protrusions may have a length protruding outwardly that is 3-10 longer than a width (extending in the axial direction) of the relatively long protrusions. The longer protrusion may provide a large step size per rotation and may improve propulsion through tubular enclosures with non-uniform diameter.

According to some example embodiments, a compliant transmission system as described herein is configured to provide movement in a forward and/or backwards direction without closed loop control and also provides a transmission ratio, which is comparable to harmonic drive but for linear propulsion. According to some example embodiments, the compliant transmission system additionally provides a holding force without rotation of the actuator, e.g. it is self-locking.

According to some example embodiments, the linear propulsion apparatus as described herein provides a significant static force when stationary and a large axial force under continuous operation. Unlike ultrasonic wave-motors, the present linear propulsion apparatus operates in a quasi-static manner by alternating between nonlinear elastic equilibria.

In some example embodiments, the compliant transmission system is suitable for propulsion through brittle enclosures such as glass tubes. Optionally, the compliant transmission has relatively low sensitivity to large tolerances in tube diameters and/or to non-uniform dimensions in a tube through which it provides propulsion and may also be suitable for propulsion along textured surfaces. Each of the components of the wave generator and the deformable sleeve may be produced at relatively low production cost and may be disposable. Optionally, the compliant transmission may also be miniaturized at low production costs. Depending on the application, the conduit may have a relatively large diameter, e.g. in applications for sewer pipes, gas pipes and power plants or may have a relatively small diameter, e.g. in application for medical devices such as pre-filled drug injection devices and automatic drug delivery systems. In some example embodiments, the conduit may be an open channel.

Figure 1:
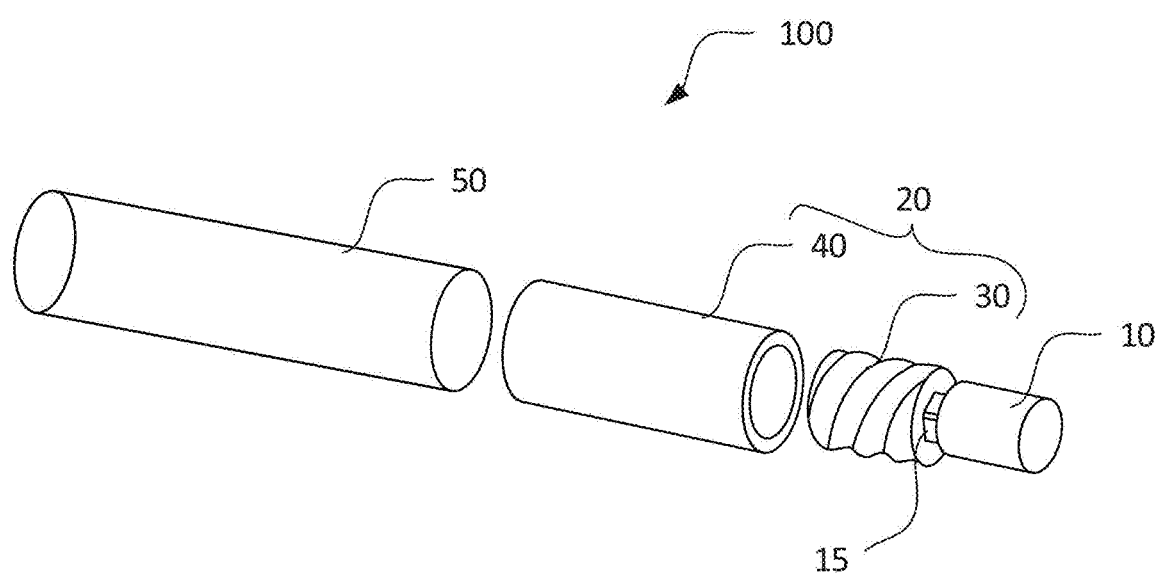

Reference is now made to FIG. 1 showing a simplified blow-up drawing of an example linear propulsion apparatus for propulsion within a conduit in accordance with some example embodiments. According to some example embodiments, a linear propulsion apparatus 100 includes a rotational actuator 10, a wave generator 30 and a deformable sleeve 40 positioned in a conduit 50 through which linear propulsion is actuated. Wave generator 30 and deformable sleeve 40 together form a compliant transmission system 20 that provides the linear propulsion based on rotation of actuator 10.

In some example embodiments, actuator 10 is fixed to wave generator 30 and may be any motor that provides rotational movement with enough torque to overcome friction between wave generator 30 and deformable sleeve 40 while the wave generator 30 is rotated within the sleeve. Optionally, actuator 10 may be a DC motor or a piezo motor. The torque required may be defined based on inner diameter of conduit 50, material forming each of wave generator 30 and deformable sleeve 40 as well as their relative diameters. According to some example embodiments, wave generator 30 includes a shaft 15 on which actuator 10 may be mounted to impart the rotational motion on wave generator 30. In alternate embodiments, actuator 10 may be an external device including a shaft that is fixedly connected to wave generator 30. In one example rotational actuator 10 may be 0.4 W motor with a speed range of 1-100 rpm that is driven by a battery and actuator 10 may be used to overcome a 40 N axial force as well as the friction due to wave generator 30 rotating within the sleeve 40.

According to some example embodiments, the wave generator 30 may be a plug including a protruding pattern that forms deformation waves on deformable sleeve 40 when rotated by the actuator 10. In some example embodiments, the pattern is a helix pattern, e.g. similar to a screw thread pattern. Wave generator 30 may be preferably formed with a rigid material that is hard enough to deform deformable sleeve 40. The height of the protruding pattern of wave generator 30 is defined to provide a desired deformation on deformable sleeve 40 and a length of wave generator 30 may be defined based on a desired range of linear motion. Wave generator 30 may be formed from a polymer, e.g. acrylonitrile butadiene styrene (ABS) or thermoplastic chlorinated polyethylene elastomer (CPE), metal or ceramic material using known manufacturing methods. Optionally, wave generator 30 may be defined to have a smooth outer surface or may be coated with a smooth material that may reduce friction with deformable sleeve 40. Optionally wave generator 30 may be configured to be disposable.

According to some example embodiments, deformable sleeve 40 may be formed from elastic material, e.g. thermoplastic polyurethane and preferably from material that maintains its elastic properties over a working range of deformations. In some example embodiments, an inner surface of sleeve 40 may be defined to be smooth so as to reduce friction with rotating wave generator 30. In some example embodiments, deformable sleeve is formed from an elastic polymer, natural rubber, silicon or a combination of these materials. In some example embodiments, deformable sleeve 40 may include a protruding pattern on its outer surface, e.g. ribs or teeth. Alternatively, deformable sleeve 40 may be configured with a smooth outer surface. Optionally, deformable sleeve 40 may be manufactured based on three-dimensional printing or molding and may be configured to be disposable.

Optionally, the compliant transmission system is also configured to operate under seemingly unfavorable conditions. Conduit 50 may be rigid tube or other tubular enclosure that may optionally be brittle and may optionally not include uniform dimensions. Diameter of conduit 50 is based on the application and may span from few millimeters to one meter. In some example embodiments, conduit 50 is glass tube that may typically be thin and include variability in its dimensions. According to some example embodiments, the compliant transmission system formed with wave generator 30 and deformable sleeve 40 is configured move through conduit 50 and to handle inaccurate dimensions typical of glass tubes and provide linear movement without breaking the glass. In some example embodiments, conduit 50 may have a textured or rough inner surface.

Figure 2:
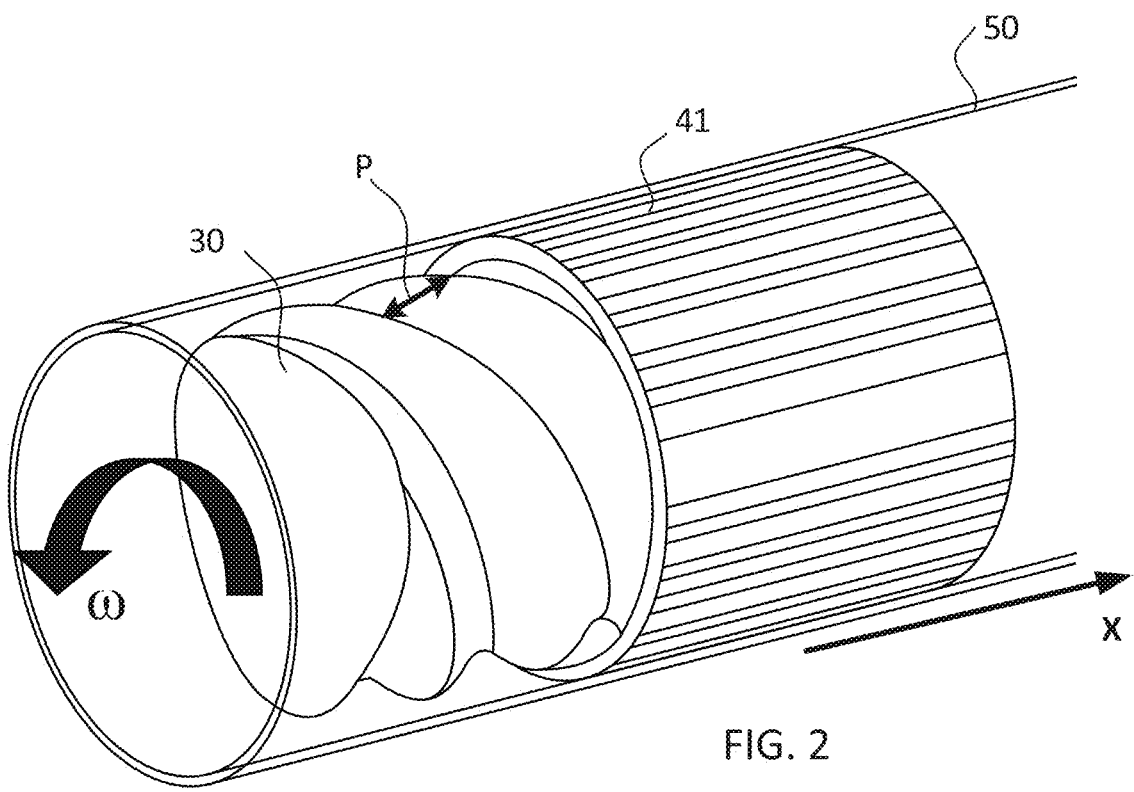

FIG. 2 is a simplified schematic drawing of an example compliant transmission system including a smooth surface deformable sleeve, in accordance with some example embodiments. An example deformable sleeve 40 is deformable sleeve 41 having a smooth outer surface. According to some example embodiments, a compliant transmission system includes deformable sleeve 41 that is pressed between wave generator 30 and a conduit 50. As wave generator 30 is rotated at a frequency, $\omega$, the helix of wave generator 30 induces a deformation waves on deformable sleeve 41. The deformation wave actuates linear movement between conduit 50 and deformable sleeve 41.

Figure 3:
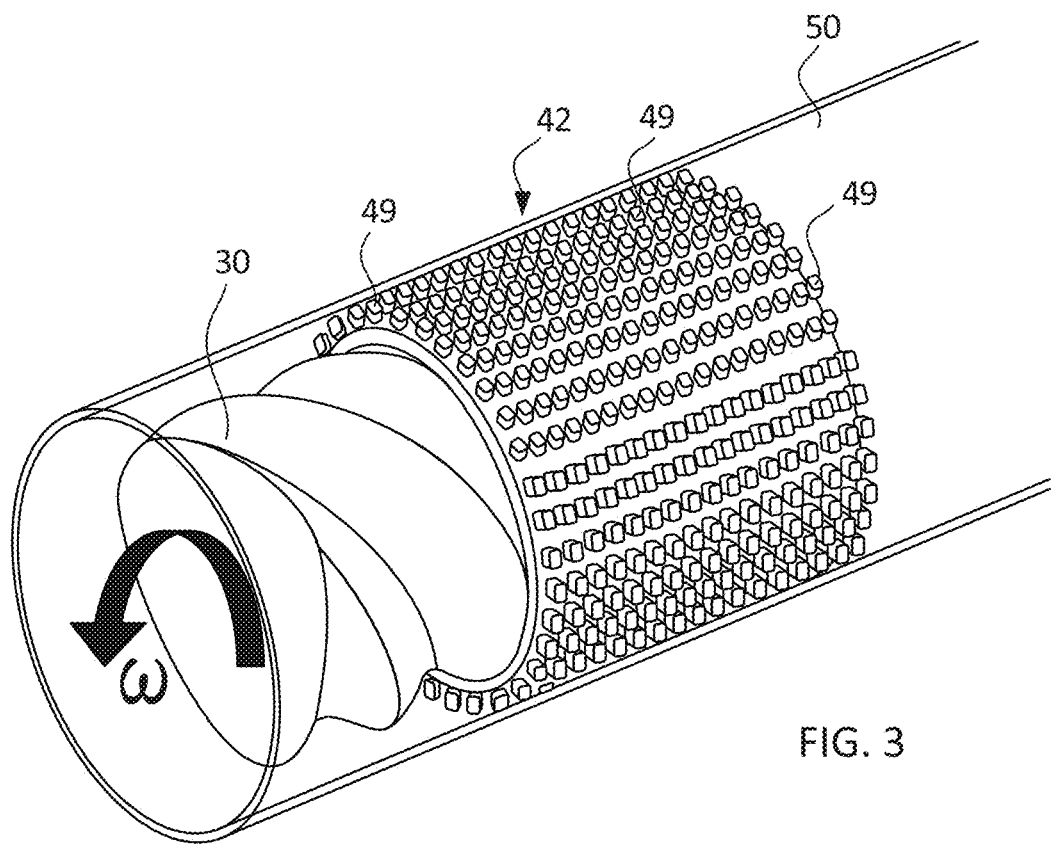

FIG. 3 is a simplified schematic drawing of an example compliant transmission system including a deformable sleeve with a patterned outer surface in accordance with some example embodiments. Another example deformable sleeve 40 is deformable sleeve 42 formed with a pattern of protruding teeth 49. Teeth 49 may be integral to deformable sleeve 42, e.g. formed from the same material as one integral part. In some example embodiments, pattern of protruding teeth 49 substantially cover at least an annular section of an outer surface of deformable sleeve 42, e.g. spread across both the longitudinal and azimuthal direction.

In some example embodiments, teeth 49 promote a larger step size as compared to a step size of a point on smooth deformable sleeve 41. As used herein a step size of a protruding element is defined as the linear displacement of one the protruding element, (e.g. tooth 49) per rotation cycle of the wave generator 30. According to some example embodiments, the pattern of protruding teeth 49 are also defined to provide a desired holding force of the compliant transmission system. Optionally, a size of teeth 49 and pitch of teeth 49 in the array is defined based on the required step size as well as the required holding force. In some example embodiments, the step size may be increased by 30-50% based on adding the pattern of flexible teeth.

Figure 4A:
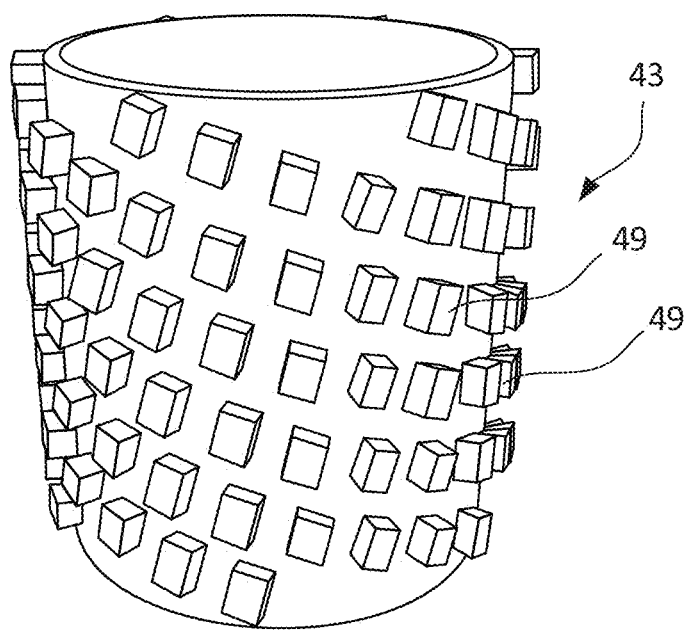
Figure 4B:
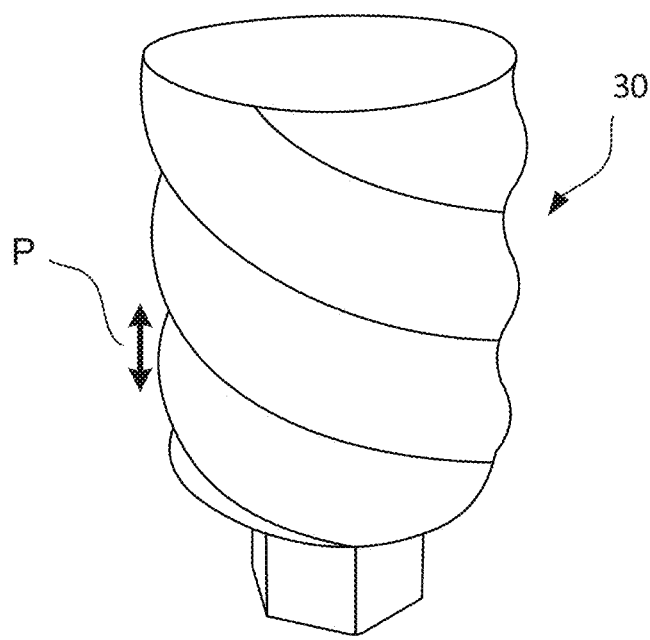

FIGS. 4A and 4B are simplified schematic drawings of an example deformable sleeve including helically arranged array of teeth and a corresponding wave generator having an example helical outer surface, both for a compliant transmission system in accordance with some example embodiments. Deformable sleeve 43 including an array of teeth 49 arranged in a helical pattern is yet another example of deformable sleeve 40. According to some example embodiments, step size of the compliant transmission system is increased based on forming deformable sleeve 43 with an array of teeth 49 arranged in a helical pattern (FIG. 4A). According to some example embodiments, the helical pattern of array of teeth 49 is defined based on correspond helix of wave generator 30 (FIG. 4B). In some example embodiments, the increase in step size as compared to a smooth exterior deformable sleeve may be a 40%-60%. The array of teeth 49 on deformable sleeve 49 may be aligned with a wave front of the wave generator to actuate simultaneous deflection of teeth 49. In other examples, the array of teeth 49 may be defined to be angled with respect to the wave front to actuate consecutive deflection of the teeth. In some example embodiments, the helical pattern on deformable sleeve 43 is configured to correspond to the helix on wave generator 30.

Figure 5A:
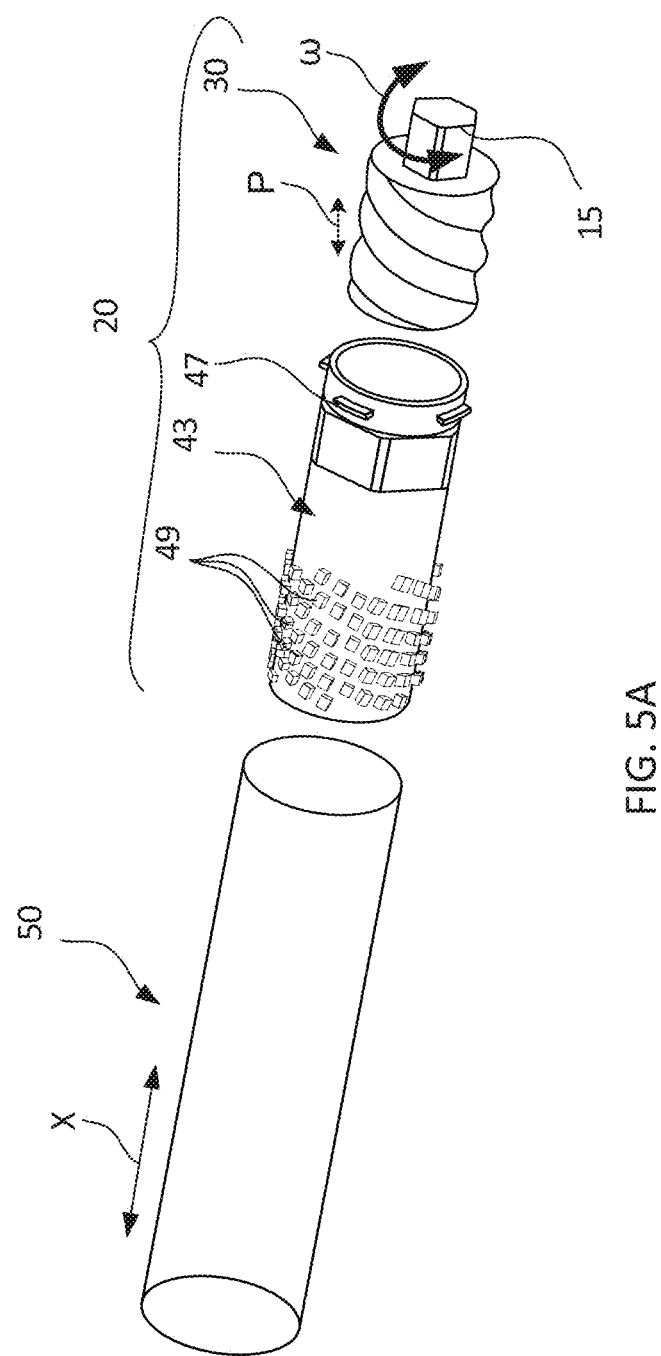

FIG. 5A is a simplified blow up schematic drawing of a tubular enclosure and an example compliant transmission system including a deformable sleeve with teeth arranged in a helical pattern in accordance with some example embodiments. According to some example embodiments, deformable sleeve 43 is pressed between wave generator 30 and a conduit 50. As wave generator 30 is rotated at a frequency, $\omega$, the helix of wave generator 30 induces deformation waves on deformable sleeve 43 that actuates linear movement of conduit 50 in an X direction (forward or backwards movement). In some example embodiments, a wavelength of the deformation wave on sleeve 43 is defined based on pitch, P, of the helix of wave generator 30. Optionally, deformable sleeve 43 may include one or more stoppers 47 that may limit a range of movement of conduit 50 with respect to deformable sleeve 43.

Figure 5B:
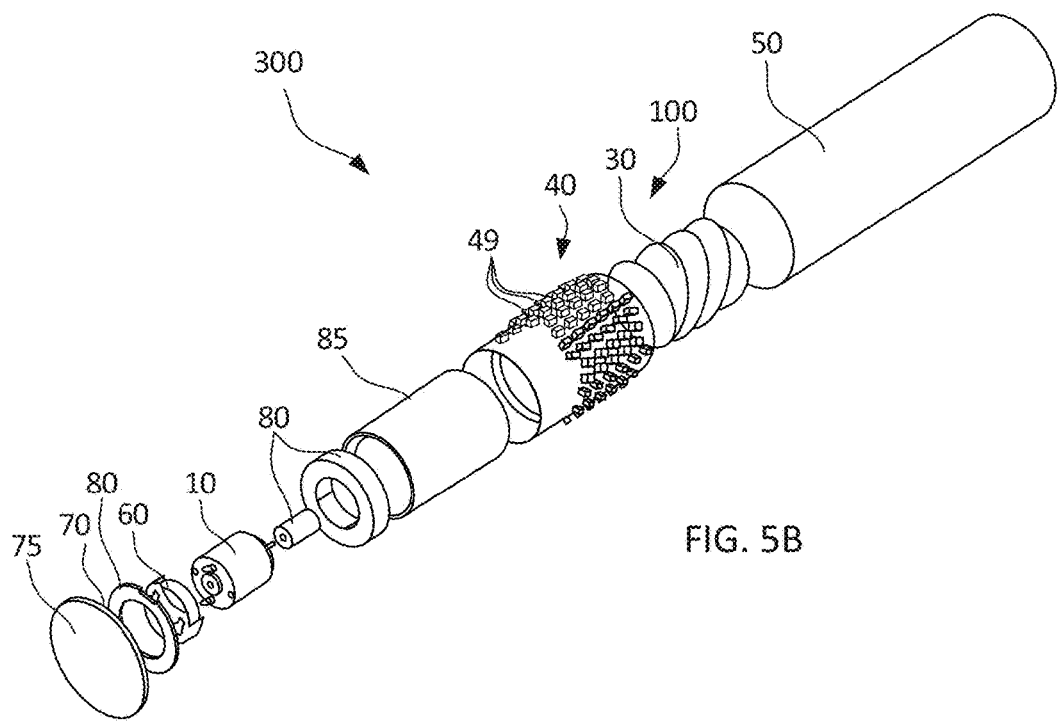
Figure 5C:
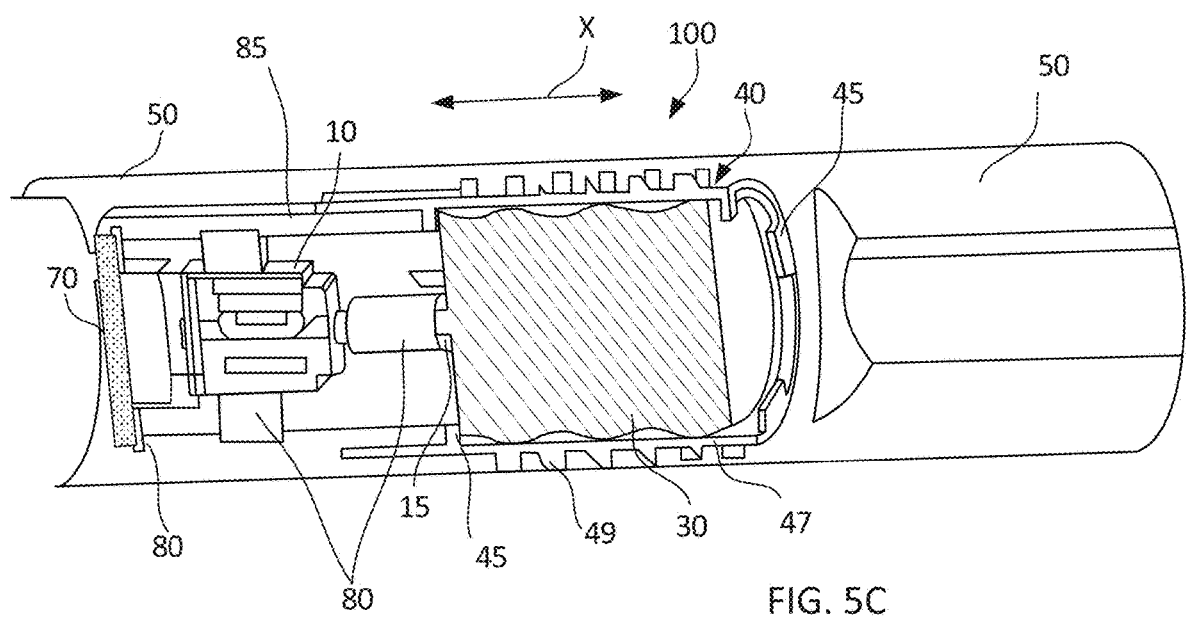

FIGS. 5B and 5C are simplified schematic blow up and cross sectional view respectively of a linear propulsion apparatus in accordance with some example embodiments. According to some example embodiments, a linear propulsion apparatus 300 is a self-propulsion apparatus including compliant transmission system 100, a rotational actuator 10, a battery 60 and circuitry 70, all sized to fit into a conduit 50. Linear propulsion apparatus 300 may linear propulsion apparatus 300 through conduit 50 and may drive an element, e.g. a plunger of a syringe.

In some example embodiments, conduit 50 is part of a syringe including a plunger and exit nozzle and linear propulsion apparatus 300 is configured to push the plunger along the syringe toward the exit nozzle. The plunger may be positioned between linear propulsion apparatus 300 and the exit nozzle. Optionally, the plunger is fixed to linear propulsion apparatus 300 and is configured to move both in a back and forth direction along with linear propulsion apparatus 300. According to some example embodiments, a propulsion apparatus 300 may be used for automated drug delivery system, e.g. for automated drug delivery through a standard syringe.

In some example embodiments, rotational actuator 10 may be mounted on shaft 15 extending from wave generator 30. Optionally, deformable sleeve 40 includes fitted over wave generator 30, includes an annular array of teeth 49 or other shaped protrusions pressed between wave generator 30 and an inner diameter of conduit 50. Examples of a deformable sleeve 40 with teeth 49 include but are not limited to sleeve 42 (FIG. 3) and sleeve 43 (FIG. 5A). In some example embodiments, wave generator 30 is positioned to overlap with array of teeth 49 and optionally maintained in place based on partition walls and/or a plurality of tabs 45 extending from an inner surface of sleeve 40 to an inner volume of sleeve 40. Tabs 45 may be configured to prevent linear motion of wave generator 30 with respect to sleeve 40.

In some example embodiments, electric components of propulsion apparatus 300 include a rotational actuator 10, a battery 60 and a circuit 70, all of which may be housed in a housing 85 that is sized to fit in conduit 50. Optionally, housing 85 is configured to be held by deformable sleeve 40. For example, a portion of sleeve 40 that does not include teeth 49 may be fitted over housing 85. One or more adaptors 80, e.g. plastic adaptors may be included to hold the electrical components in place within housing 85 and/or to provide coupling between the electrical components. Optionally, motor 10 is fixed to housing 85 with an adaptor 80 to prevent its rotation within housing 85. In some example embodiments, housing 85 is fixed to sleeve 40 and moves within conduit 50 (or with respect to conduit 50) along with sleeve 40.

In some example embodiments, circuit 70 includes a plurality of components optionally mounted on a printed circuit board (PCB). Circuit 70 may operate as a controller of the linear propulsion apparatus. Optionally, circuit 70 includes a wireless communication unit, e.g. blue tooth configured to communicate with an external controller. Operation of propulsion apparatus 300 may be controlled based on circuit 70 and/or based on an external controller in communication with circuit 70, e.g. wireless communication unit included in circuit 70.

Figure 6:
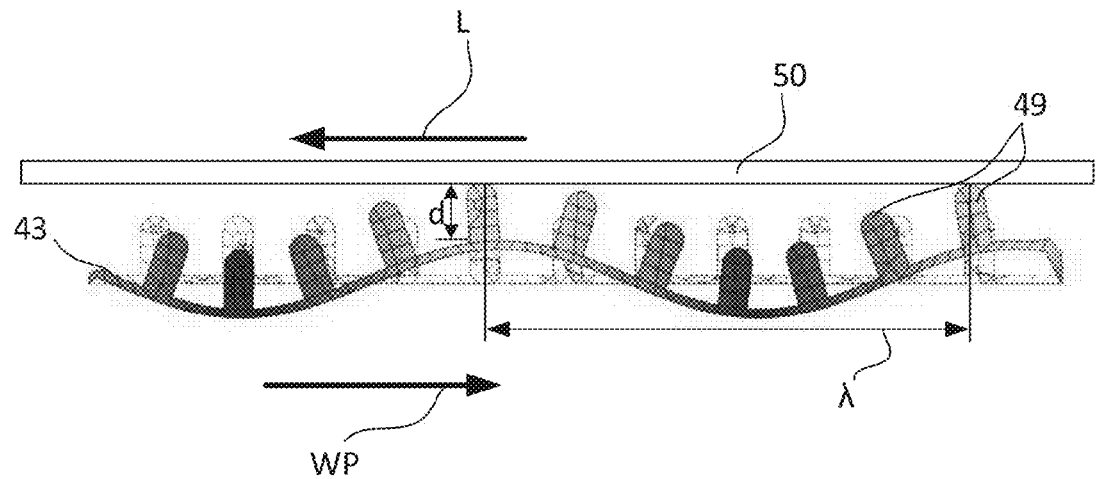

FIG. 6 is a simplified schematic drawing showing an example wave motion of a portion of the compliant transmission system actuating linear self-propulsion within a conduit in accordance with some example embodiments. According to some example embodiments, a deformation wave with wavelength λ, induced on deformable sleeve 43 may propagate in a direction WP and may actuate linear motion of conduit 50 in a direction L opposite direction WP. As the deformation wave is propagated various teeth 49 engage with an inner surface of conduit 50 at various times and push conduit 50 in a direction L. Optionally, the wave equation for deformation wave along the X direction and over time t may be defined by:

$$w(x, t) = a \cdot \sin\left(\frac{(2\pi x - p\omega t)}{\lambda}\right) \qquad \text{Equation (1)}$$

Where:
a=wave amplitude;
p=pitch
λ=wave length of deformation wave; and
ω=rotational frequency.

Figure 7:
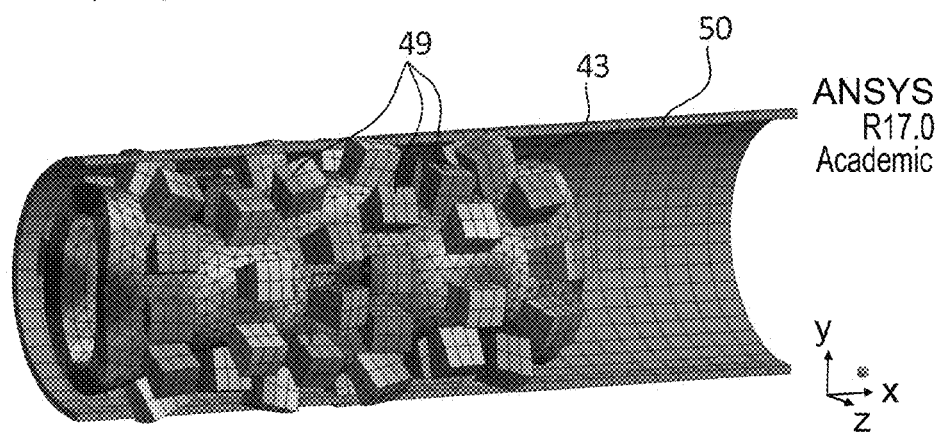
Figure 7:
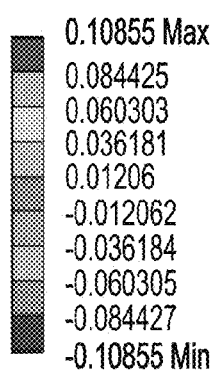

FIG. 7 is a simplified schematic drawing showing a simulation demonstrating deformations of an elastic sleeve based on the azimuthal orientation of the helix within the elastic sleeve in accordance with some example embodiments. According to some example embodiments, as a deformation wave is propagated along deformable sleeve 43, some teeth 49 engage walls of conduit 50 while other teeth are displaced from conduit.

In some example embodiments, axial movement (along an X direction) of each tooth while the helix rotates may be defined by the following equation:

$$DX = \frac{4\pi a d}{\lambda} \qquad \text{Equation (2)}$$

where
DX is the axial movement (along an X direction); and
d is a length of tooth 49 or its distance from a neutral axis of the deformable sleeve 43. Optionally, length of tooth 49 may be 0.5-3 times a width (or diameter) of tooth 49.

In the absence of slippage, DX may be the axial motion of a tooth 49 per revolution of the helix. Since several teeth are in contact with conduit 50 at any one time, some slip may be expected. Motion of deformable sleeve with respect to conduit 50 is composed of a summation of forces between teeth 49 on conduit 50 during rotation of the wave generator.

In one example, a compliant transmission system may be selected to impress a wave with wavelength λ=10 mm and amplitude a=0.2 mm on deformable sleeve 43. Optionally, deformable sleeve 43 includes an array of teeth with length (or height) d=1.0 mm. In this example, DX is 0.25 millimeters per revolution based on Equation (2). The present inventors have found that such a compliant system may be driven with a 0.4 W motor with a speed range of 1-100 rpm. The motor with the compliant system may be suitable to overcome a 40 N axial force as well as the friction due to wave generator 30 rotating within the sleeve 40.

Figure 8A:
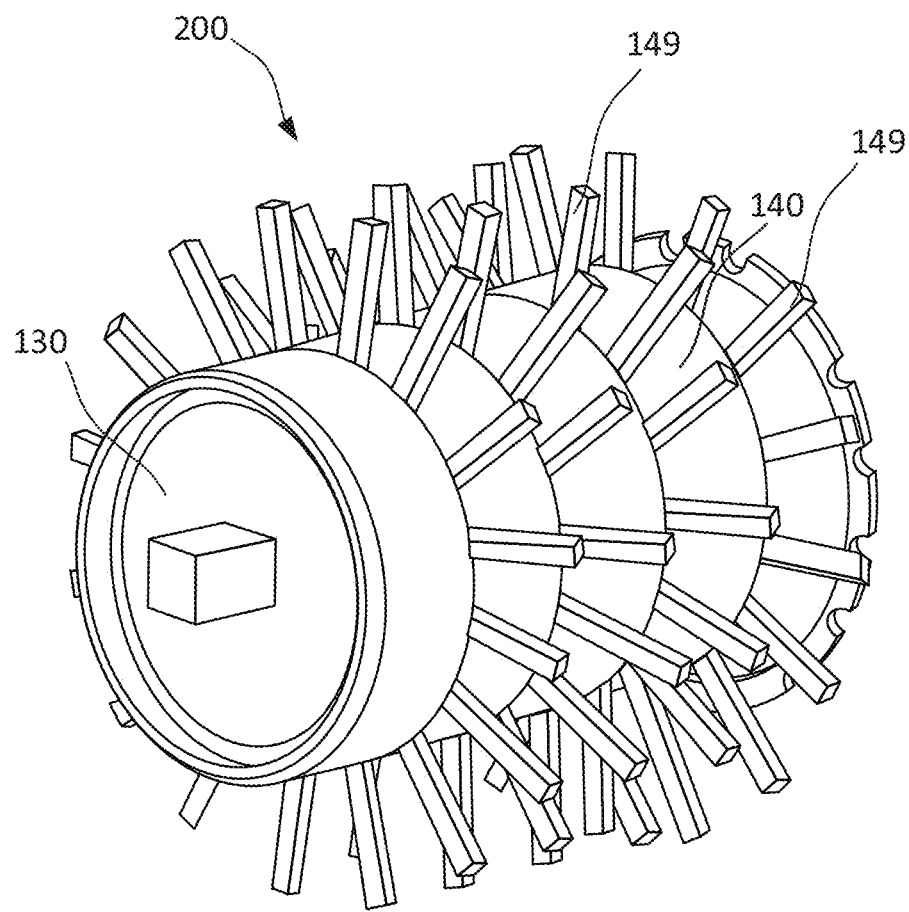
Figure 8B:
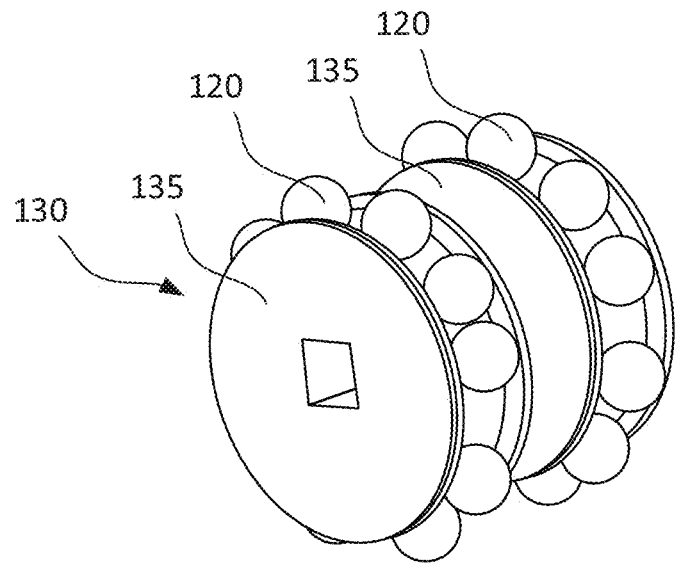
Figure 8C:
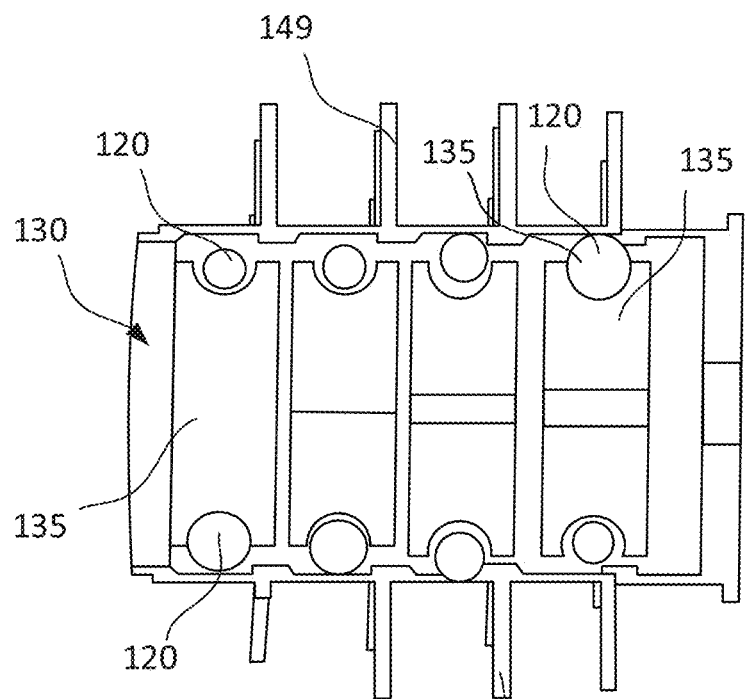

FIGS. 8A, 8B and 8C are simplified schematic drawings an example compliant transmission system including a cam shaft in accordance with some example embodiments. According to some example embodiments, a compliant transmission system 200 may include a deformable sleeve 140 include long protruding elements such as legs 149 in place of teeth 49. Optionally, legs 149 may be 2-10 or 3-10 times longer than teeth 49 depending on diameter and material properties of leg 149. Optionally, legs 149 may exhibit greater deformation based on the rotating wave generator 130. Deformable sleeve with legs 149 may be formed with same material that may be used to form deformable sleeve 40. Optionally, legs 149 may be bent when placed inside a conduit and may have a larger surface area of contact with the conduit. The larger contact area may increase the force applied by legs 149 in the axial direction. Optionally, the relative longer legs 149 as compared to teeth 49 afford more axial motion per rotation of the wave generator 200. For example, based on equation (2) increasing length of legs 149 (parameter d in Equation (2)) the axial movement (DX) is increased. Legs protrusions 149 are more flexible as compared to the teeth protrusions 49 and may be more suitable for providing larger steps sizes per revolution but with relatively lower axial force, e.g. an axial force of 0.5-10 N or 1-2 N. The shorter teeth protrusion 49 may be more suitable for overcoming larger axial forces, e.g. axial forces that may be present in a syringe.

According to some example embodiments, wave generator 130 may generate a wave based on a camshaft including an array of cams 135 each have a defined shape and together forming a deformation wave. Optionally, cams 135 include bearings 120 to reduce friction between the cams 135 and deformable sleeve 140.

Figure 9A:
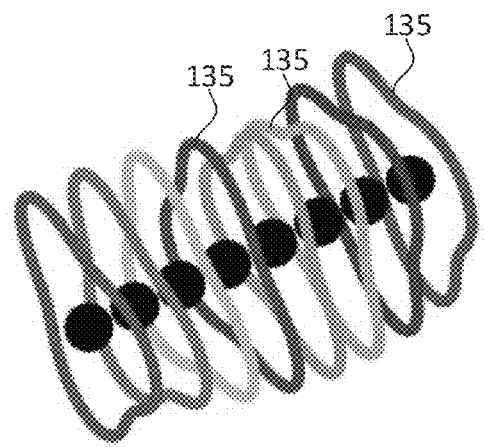
Figure 9B:
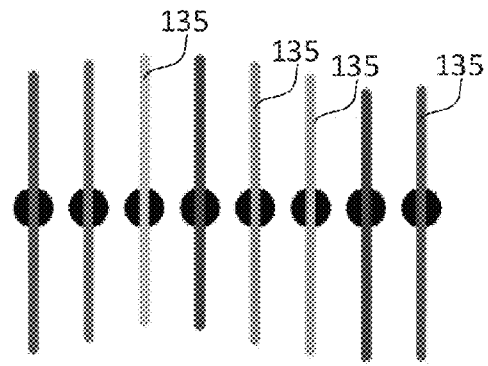

FIGS. 9A and 9B are schematic drawings of an array of cams shown in a perspective view and a side view, respectively, both in accordance with some example embodiments. In some example embodiments, a shape of each of cams 135 together with their relative phase rotation may define an envelope sinusoidal wave (FIG. 9B). Optionally, based on movement of the array of cams 135, legs 149 move in an elliptical path.

Figure 10:
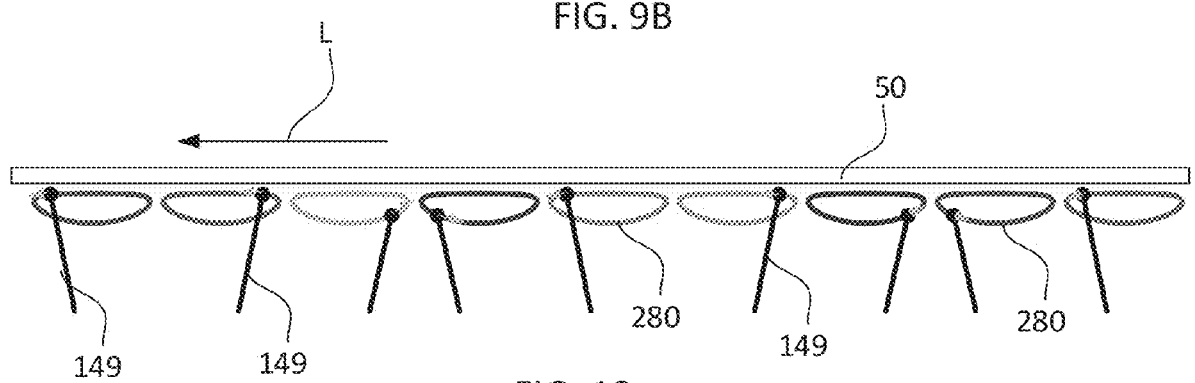

FIG. 10 is a schematic drawing of example elliptical paths that tips of legs on an outer surface of a deformable sleeve may create while moving along a surface in accordance with some example embodiments. According to some example embodiments, wave generator 130 generates a defined deformation wave that move legs 149 in an elliptical path 280. Optionally, elliptical path 280 is flattened in a vicinity of the conduit 50. Due to the extended shape of legs 149, a period of contact between conduit 50 and a leg 149 may be increased as compared to contact of teeth 49. The increase in the period of contact may increase step size provided by legs 149.

It is noted that although most of the embodiments of the compliance transmission system and the linear propulsion apparatus has been described as being operated or designed to be operated in a tubular enclosure, it is understood that the compliance transmission system and the linear propulsion apparatus may also be used to provide linear movement in an open channel or on a flat surface.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. In addition, any priority document(s) of this application is/are hereby incorporated herein by reference in its/their entirety.

Various embodiments and aspects of the present invention as delineated hereinabove and as claimed in the claims section below find experimental and/or calculated support in the following examples.

EXAMPLES

Reference is now made to the following examples, which together with the above descriptions illustrate some embodiments of the invention in a non limiting fashion.

Example 1

FIGS. 11A and 11B are an image of an experimental setup (FIG. 11A) to track linear propulsion with an example linear propulsion apparatus, and corresponding detected results (FIG. 11B) in accordance with some example embodiments. In the example experimental setup a wave generator 30 and deformable sleeve 43 is fitted in a glass tube 50. Rotation of wave generator 30 is actuated by a motor connected to shaft 20. Glass tube 50 is stabilized to prevent its rotation. An elastic band 330 was positioned on glass tube 50 and its position along a Y direction at a point in window 310 was tracked. The output is shown in FIG. 11B. As can been seen smooth linear motion was achieved both in the forward and backwards direction.

Example 2

FIGS. 12A, 12B and 12C are an image of another experimental setup to track linear propulsion with an example linear propulsion apparatus (FIG. 12A), and corresponding detected results (FIGS. 12B and 12C) in accordance with some example embodiments. The example experimental setup is similar to that discussed in reference to FIG. 11A except that displacement was tracked in a window 320 at a bottom of tube 50. FIG. 12C tracks the rotation pulse that was applied to drive the displacement shown in FIG. 12B. As can be seen in FIG. 12C, rate of rotation was increased over the period between 30-60 seconds. As can be seen, the linear propulsion was steady even as the rotational speed of the motor was increased.

Example 3

FIGS. 13A, 13B, 13C and 13D are example graphs showing axial motion as a function of shaft rotations for two different rotation profiles, all in accordance with some example embodiments. A first shaft rotation profile shown in FIG. 13A depicts shaft rotations that steadily increase in a linear fashion from 0 to 8 over a period of 60 seconds. A second shaft rotation profile shown in FIG. 13C depicts shaft rotations that increase in a nonlinear fashion from 0 to 16 over a same period of 60 seconds. Corresponding axial motions shown in FIGS. 13B and 13D respectively show that the motion is independent from the rotation speed.

Example 4

FIG. 14A is a schematic drawing of an example compliant transmission system including four cam sections, and an example graph showing effect of relative rotation (phase shift) between each of the four cam sections on the uniformity of the motion, all in accordance with some example embodiments. In FIG. 14A, a sleeve 140 is fitted over the four cam sections and each cam section is aligned with dedicated array of legs 149 of the sleeve that are annularly arranged around the sleeve. FIG. 14B is an example graph showing the effect of relative rotation (phase shift) between each of the four cam sections. As can be seen, uniform motion may be achieved based on defining a phase shift that reduces the variation of force. For example a phase shift of 29.3 degrees was shown to provide more uniform motion as compared to a phase shift of 42.8 degrees.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A compliant transmission system comprising:
a rotatable wave generator having on an external surface thereof a pattern extending both annularly and in a longitudinal direction; and
a sleeve fitted on the wave generator, wherein the sleeve is configured to deform elastically and to be impressed on its outer surface with waves extending along the longitudinal direction during rotation of the wave generator including said pattern within the sleeve.

2. The compliant transmission system according to claim 1, being sized to fit into a tubular enclosure, wherein the outer surface of the sleeve is in physical contact with an inner wall of the tubular enclosure, wherein the wave impressed on the sleeve and the contact of the sleeve with the inner wall of the tubular enclosure are selected to impart a relative linear motion between the enclosure and the compliant transmission system and wherein the physical contact between the sleeve and the inner wall is configured to lock the complaint transmission system in place absent rotation of the wave generator.

3. The compliant transmission system according to claim 1, wherein the wave generator is a rod shaped element, and wherein the pattern comprises a raised helical thread extending around the rod and in the longitudinal direction.

4. The compliant transmission system according to claim 1, wherein the wave generator comprises a connector configured to fixedly connect with a rotational actuator.

5. The compliant transmission system according to claim 1, wherein the wave generator is formed of a rigid material.

6. The compliant transmission system according to claim 1, wherein the wave generator is formed of a polymer material.

7. The compliant transmission system according to claim 1, wherein the outer surface of the sleeve includes a pattern of protruding teeth, wherein the pattern of protruding teeth extends along both the longitudinal direction and an azimuth direction and is a helix.

8. The compliant transmission system according to claim 1, wherein the wave generator comprises an array of cams positioned on an axle and wherein the relative phase angle between the array of cams is configured to define the pattern on the external surface of the wave generator, wherein each of the cams in the array includes bearings fitted on the outer surface of the wave generator to reduce the friction between the wave generator and the sleeve during rotation and wherein the sleeve includes a pattern of elongated protruding elements extending from an outer surface of the sleeve, wherein a length of the elongated protruding elements extending from the outer surfaces is 3-10 times longer than a diameter of the protruding elements.

9. A linear propulsion apparatus comprising: the compliant transmission system according to claim 1; and a rotational actuator coupled to the complaint transmission system.

10. The linear propulsion apparatus according to claim 9, being configured to impart a relative linear motion between a tubular enclosure and the compliant transmission system and wherein both the compliant transmission system and the rotational actuator are sized to fit into the tubular enclosure.

11. The linear propulsion apparatus according to claim 10, wherein the rotational actuator is external to the tubular enclosure and coupled to the wave generator with an axle mounted on the rotational actuator.

12. The linear propulsion apparatus according to claim 9, being configured to be a self-propulsion apparatus, wherein the rotational actuator is sized to be contained within the tubular enclosure.

13. The linear propulsion apparatus according to claim 9, wherein the rotational actuator is a direct current (DC) motor or piezo motor.

14. A disposable drug delivery system comprising:
a tubular enclosure containing a drug to be delivered;
a movable wall configured to displace the drug contained in the tubular enclosure;
an outlet through which the drug contained in the tubular enclosure is dispensed; and
a linear propulsion apparatus according to claim 9 configured to move the movable wall.

15. The disposable drug delivery system according to claim 14, wherein the tubular enclosure, the movable wall and the outlet are elements of a syringe, and wherein the linear propulsion apparatus is configured to drive dispensing of the drug through the syringe.

16. The disposable drug delivery system according to claim 14 wherein the linear propulsion apparatus is a self-propulsion apparatus.

17. The disposable drug delivery system according to claim 14, being configured to be implantable in a human body.

18. The disposable drug delivery system according to claim 14, wherein the tubular enclosure is a glass tube.

19. A method of linear propulsion within a tubular enclosure, the method comprising:
positioning a compliant transmission system into a tubular enclosure, wherein the compliant transmission system comprises a wave generator and a sleeve fitted on the wave generator, wherein the both the wave generator and the sleeve extend in a longitudinal direction and wherein an outer surface of the sleeve is flush with an inner surface of the tubular enclosure;
rotating the wave generator with respect to the sleeve;
generating waves on the sleeve that extend along the longitudinal direction; and
inducing relative linear motion between the sleeve and the tubular enclosure based on the waves that have been generated.

20. The method according to claim 19, comprising fixating the tubular enclosure to an external structure such that the wave pattern on the outer surface of the sleeve effects linear motion of the sleeve within the enclosure without effecting rotation or translation on the enclosure.

21. The method according to claim 19, wherein the wave generator is rotated with a rotational actuator that is positioned within the tubular enclosure.

22. A compliant transmission system comprising:
a rotatable wave generator, being formed of a rigid material and having on an external surface thereof a pattern extending both annularly and in a longitudinal direction; and
a sleeve fitted on the wave generator, wherein the sleeve is configured to be deformable and to be impressed on its outer surface with waves extending along the longitudinal direction during rotation of the pattern of the wave generator within the sleeve.

23. A compliant transmission system comprising:
a rotatable wave generator having on an external surface thereof a pattern extending both annularly and in a longitudinal direction; and
a sleeve fitted on the wave generator, wherein the sleeve is configured to be deformable and to be impressed on its outer surface with waves extending along the longitudinal direction during rotation of the pattern of the wave generator within the sleeve;
wherein the outer surface of the sleeve includes a pattern of protruding teeth, wherein the pattern of protruding teeth extends along both the longitudinal direction and an azimuth direction and is a helix.

24. A compliant transmission system comprising:
a rotatable wave generator having on an external surface thereof a pattern extending both annularly and in a longitudinal direction; and
a sleeve fitted on the wave generator, wherein the sleeve is configured to be deformable and to be impressed on its outer surface with waves extending along the longitudinal direction during rotation of the pattern of the wave generator within the sleeve;
wherein the wave generator comprises an array of cams positioned on an axle and wherein the relative phase angle between the array of cams is configured to define the pattern on the external surface of the wave generator, wherein each of the cams in the array includes bearings fitted on the outer surface of the wave generator to reduce the friction between the wave generator and the sleeve during rotation and wherein the sleeve includes a pattern of elongated protruding elements extending from an outer surface of the sleeve, wherein a length of the elongated protruding elements extending from the outer surfaces is 3-10 times longer than a diameter of the protruding elements.

25. A disposable drug delivery system comprising:
a tubular enclosure containing a drug to be delivered;
a movable wall configured to displace the drug contained in the tubular enclosure;
an outlet through which the drug contained in the tubular enclosure is dispensed; and a linear propulsion apparatus configured to move the movable wall, said linear propulsion apparatus comprising a compliant transmission system and a rotational actuator coupled to the complaint transmission system;

wherein said compliant transmission system comprises: a rotatable wave generator having on an external surface thereof a pattern extending both annularly and in a longitudinal direction, and a sleeve fitted on the wave generator, wherein the sleeve is configured to be deformable and to be impressed on its outer surface with waves extending along the longitudinal direction during rotation of the pattern of the wave generator within the sleeve.

* * * * *